United States Patent
Stets et al.

[11] Patent Number: 5,679,904
[45] Date of Patent: Oct. 21, 1997

[54] METHOD AND TEST PLUG FOR FIELD TESTING PIPE JOINTS

[75] Inventors: Joseph A. Stets, Gahanna; Sudheer M. Pimputkar, Columbus, both of Ohio

[73] Assignee: Gas Research Institute, Chicago, Ill.

[21] Appl. No.: 640,282

[22] Filed: Apr. 30, 1996

[51] Int. Cl.[6] .............. G01L 5/00; G01N 3/08
[52] U.S. Cl. .............. 73/827; 73/862.542; 73/46
[58] Field of Search .............. 73/40, 46, 49.8, 73/826, 827, 831, 832, 862.542

[56] References Cited

U.S. PATENT DOCUMENTS

| | | | |
|---|---|---|---|
| 2,462,575 | 2/1949 | Walker | 285/108 |
| 2,572,613 | 10/1951 | Goff | 85/1 |
| 2,682,796 | 7/1954 | Larson | 81/52.5 |
| 3,213,673 | 10/1965 | Schulhoff, Sr. | 73/49.2 |
| 3,229,711 | 1/1966 | Leopold, Jr. et al. | 137/459 |
| 3,444,732 | 5/1969 | Robbins et al. | 73/150 |
| 3,479,072 | 11/1969 | Kosar | 287/52.08 |
| 3,501,993 | 3/1970 | Swenson et al. | 85/1 |
| 3,738,163 | 6/1973 | McEntire | 73/862.542 |
| 3,826,646 | 7/1974 | Karlsson et al. | 75/13 |
| 3,952,691 | 4/1976 | Peltz et al. | 16/65 |
| 3,978,881 | 9/1976 | Mouranie | 137/318 |
| 4,025,371 | 5/1977 | Pecha | 156/64 |
| 4,040,289 | 8/1977 | Clark et al. | 73/46 |
| 4,078,833 | 3/1978 | Carter | 285/24 |
| 4,352,708 | 10/1982 | McElroy | 156/378 |
| 4,467,636 | 8/1984 | Dagn | 73/49.8 |
| 4,513,605 | 4/1985 | Hawerkamp | 73/40 |
| 4,533,424 | 8/1985 | McElroy | 156/378 |
| 4,657,626 | 4/1987 | Cearlock et al. | 156/580 |
| 4,664,001 | 5/1987 | Denman | 81/479 |
| 4,712,809 | 12/1987 | Legris | 285/21 |
| 4,753,115 | 6/1988 | Moody | 73/826 X |
| 4,759,225 | 7/1988 | Reynertson et al. | 73/862.21 |
| 4,791,839 | 12/1988 | Bickford et al. | 81/479 |
| 4,809,735 | 3/1989 | Volgstadt et al. | 137/318 |
| 4,822,203 | 4/1989 | Walmsley | 403/314 |
| 4,899,684 | 2/1990 | Houzvic et al. | 116/272 |
| 4,940,259 | 7/1990 | Williams et al. | 285/3 |
| 4,949,744 | 8/1990 | Heed | 137/15 |
| 4,951,697 | 8/1990 | Fritts | 137/68.1 |
| 4,958,541 | 9/1990 | Annis et al. | 81/479 |
| 5,172,616 | 12/1992 | Negishi | 81/467 |
| 5,394,775 | 3/1995 | Fagerstrom | 81/479 |

FOREIGN PATENT DOCUMENTS

| | | |
|---|---|---|
| 2829009 | 1/1980 | Germany . |
| 3318910 | 11/1984 | Germany . |
| 0755544 | 8/1980 | U.S.S.R. . |
| 0770611 | 3/1957 | United Kingdom . |

*Primary Examiner*—Michael Brock
*Attorney, Agent, or Firm*—Greer, Burns & Crain, Ltd.

[57] ABSTRACT

A fusion joint test system for a saddle fusion joint on a pipe includes a test plug having a rotatable swivel base with a hard rubber foot for accommodating the curvature of the pipe, and for preventing the base from rotating once it comes in contact with the pipe. The base is connected to a threaded shank that engages the internal threads of a cylindrical bore of a connector that forms the saddle. The shank has a top end for receiving an electronic torque wrench. The torque wrench applies a predetermined torque on the plug, which exerts an upward force on the saddle joint. The shank may also have an air channel for also allowing fluid pressure to be applied to the fusion joint.

7 Claims, 2 Drawing Sheets

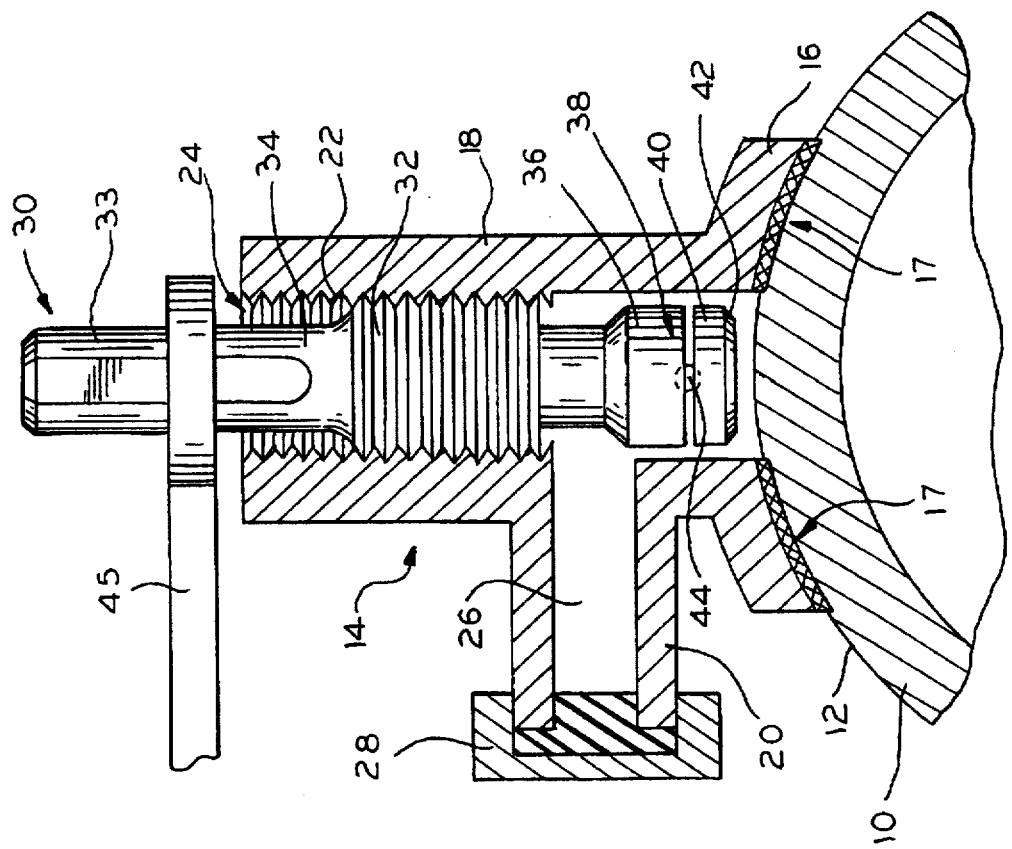
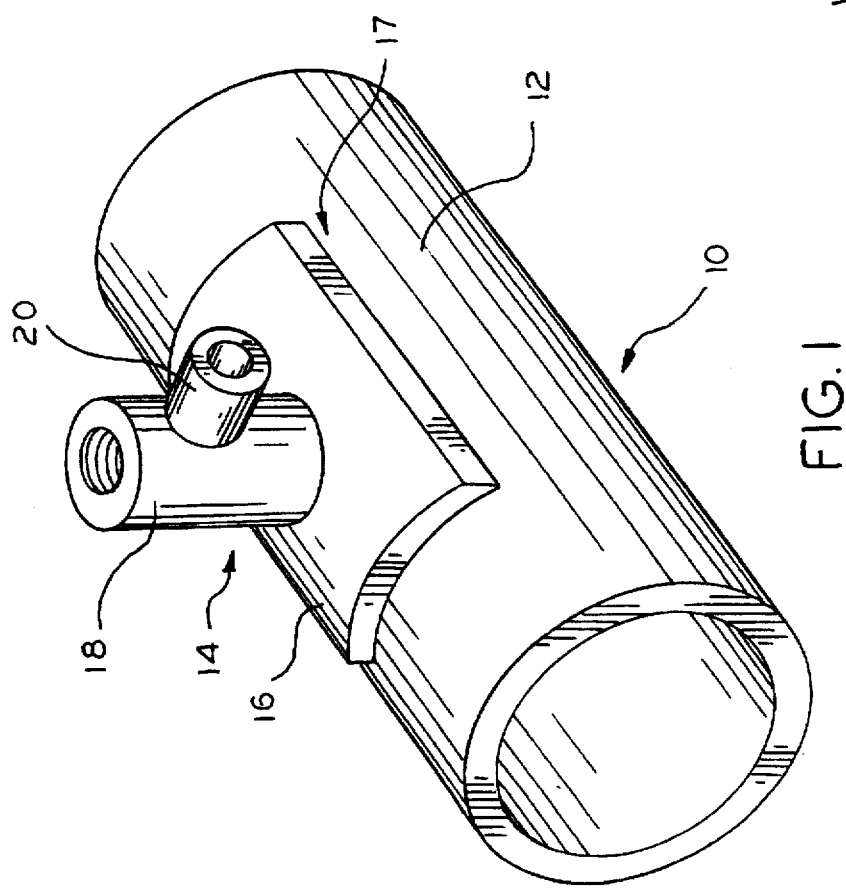
FIG. 1
FIG. 2

METHOD AND TEST PLUG FOR FIELD TESTING PIPE JOINTS

This invention relates generally to methods and apparatus for testing pipe joints, and more particularly, to methods and apparatus for testing saddle fusion joints prepared on site when tapping into existing plastic pipe gas distribution pipelines.

CROSS REFERENCE TO RELATED APPLICATION

This application is related to a patent application entitled: "Pneumatic Fusion Joint Test System And Method" filed on Apr. 30,1996 and assigned Ser. No. 08/640,281 with the same inventors as the instant application.

BACKGROUND OF THE INVENTION

Currently, plastic pipe gas distribution pipelines, such as polyethylene (PE) pipelines, are tapped on site for service lines by heat fusing a T-connector to the main pipeline. The T-connector has a saddle portion which is fused to an outer surface of the pipe forming a saddle fusion joint. An elongated threaded opening in the T-connector houses a threaded cutter that taps a hole in the pipe and serves as a shut off valve after the pipe is tapped. A service line outlet is provided in the side of the elongated threaded portion for releasing gas from the pipeline when the cutter is unthreaded.

The threaded cutter includes a threaded upper portion which cooperates with the internal threads of the threaded opening, and a lower portion with a sharp, thin, metal annulus which acts as the cutting edge. After the saddle portion is fused to the main pipeline, the cutter screws into the pipe surface so that the sharp edge cuts through the pipe wall. The cutter is then partially unscrewed and may be used as a valve to control gas flow.

However, as the cutter is screwed into the main pipeline, an upward force is exerted on the fused interface or fusion joint. If the saddle fusion joint is weak or faulty, the joint may become partially or completely detached from the pipe, possibly causing a leak. This can raise serious safety concerns. Also, a faulty joint after cutting or during cutting may leave the main pipeline with an unserviceable, partially or completely cut hole. This makes repair very difficult, particularly if gas is leaking from the pipe.

Thus, there is a need for methods and apparatus for testing the fusion interface joint before cutting the pipe. Accordingly, one object of this invention is to provide methods and apparatus for testing pipe fusion joints that include a plug device for applying a predetermined test force to the pipe joints to determine the integrity of the joint.

Still, another object is to provide methods and apparatus for testing fusion joints in pipes before the pipe is cut wherein unnecessary damage to the surface of the pipe is substantially avoided.

Yet another object is to provide methods and apparatus for testing fusion joints in pipes wherein the application of both fluid pressure and mechanically applied forces are used to test the integrity of a pipe fusion joint.

SUMMARY OF THE INVENTION

In keeping with one aspect of this invention, a test plug for testing a fusion joint is provided having a swivel base. The test plug includes a threaded portion which mates with the threaded portion of the T-connector, a shank on one end for engaging and disengaging the threads with a torque application device, and a swivel base on the other end of the threaded portion. The swivel base preferably has a rubber foot at a bottom thereof to avoid unnecessary damage to the outer surface of the pipe during testing.

In use, the T-connector, preferably a saddle, is heat fused to the pipe before a hole is cut in the pipe. Before the hole is cut, the test plug is threaded into the threaded portion of the saddle. When the rubber foot is pressed against the surface of the pipe, the swivel allows the plug to be tightened without rotating the rubber foot, so that the pipe is not damaged. As the plug is tightened, mechanical force is placed on the saddle fusion joint. A weak or defective joint can be detected by applying this force on it. The amount of force placed on the joint is predetermined, and is controlled by a torque detection mechanism such as a settable torque application device or other suitable device.

In keeping with another aspect of the invention, both a mechanical force and fluid pressure is applied to the fusion joint. A disclosed pneumatic test plug includes a swivel base and fluid channel or passages through the threaded portion. A valve mechanism coupled with the fluid channel prevents fluid, such as air, gas or water, from escaping during testing. The fluid channel may extend axially through the shank and radially adjacent the swivel head to allow fluid to be forced on the fusion joint through an isolated area about the head.

In use, the pneumatic test plug is tightened to a predetermined torque and a fixed amount of fluid pressure is applied through the fluid channel into the area surrounding the swivel head to apply a force on the fusion joint. A pressure gauge coupled to the channel is analyzed to determine if the pressure drops over time. Loss of pressure indicates a leaky fusion joint.

A method of testing a pipe fusion joint is also disclosed which includes the steps of: screwing a swivel test plug into the internally threaded cylindrical bore of the threaded T connector until the plug makes contact with the pipe; tightening the test plug with a predetermined torque to exert a force on the fusion interface, such as an upward force; and inspecting the fusion interface for an interface failure.

Another disclosed method of testing a pipe fusion joint includes the use of both mechanically exerted force and fluid pressure. One such described method includes: screwing the swivel test plug into the internally threaded cylindrical bore of the connector housing until the plug makes contact with the pipe; tightening the test plug with a predetermined torque to exert an upward force on the fusion interface; applying a predetermined amount of fluid pressure through the swivel test plug to apply pressure to the saddle fusion joint; and inspecting the fusion interface for an interface failure.

BRIEF DESCRIPTION OF THE DRAWINGS

The above objects and features of the present invention will be more apparent from the description of the preferred embodiments with reference to the accompanying drawings.

FIG. 1 is a perspective view generally depicting a T-connector saddle, heat fused onto a main pipe;

FIG. 2 is a partial cross-sectional view of a conventional T-connector saddle heat fused to a main pipe with an embodiment of a swivel test plug in accordance with one embodiment of the invention;

DETAILED DESCRIPTION

Figure 4:
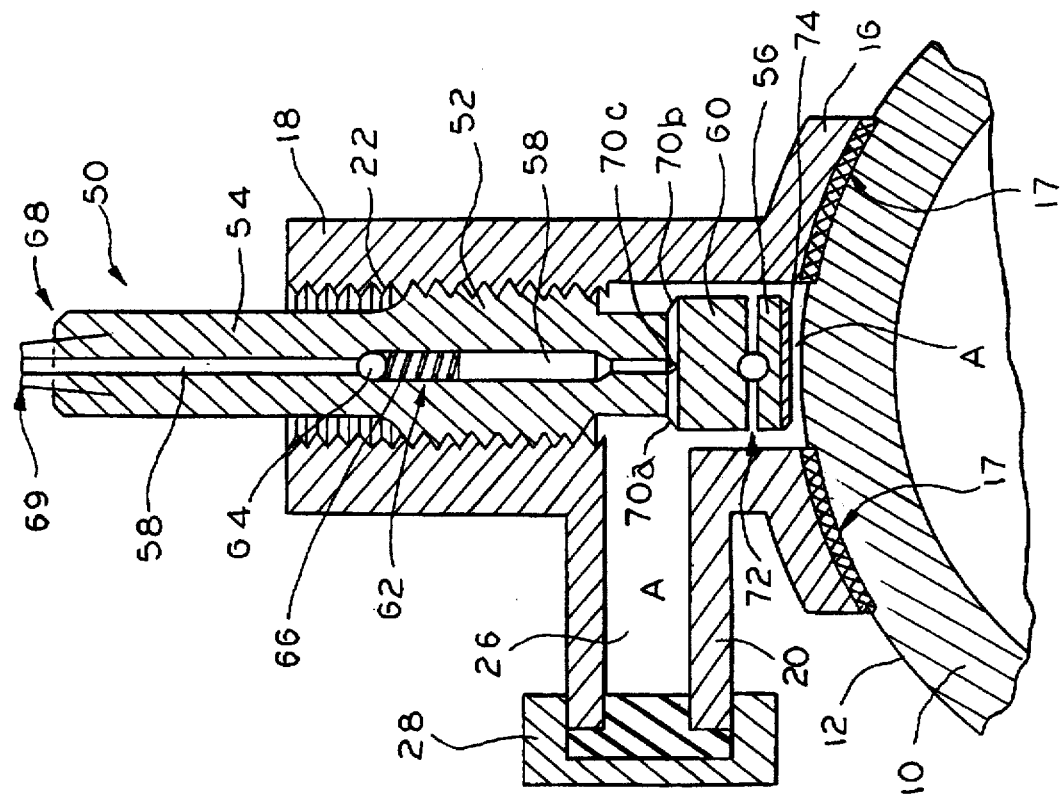
FIG. 4 is a partial cross-sectional view of a conventional saddle T-connector heat fused to a main pipe with an embodiment of a pneumatic swivel test plug in accordance with the invention.

As seen in FIG. 1, a pipe 10 has an outer surface 12. A T-connector 14, such as a service saddle connector, is heat fused to the surface 12 around the outer periphery of a saddle 16 to form a saddle fusion joint 17. A threaded portion 18 extends from the saddle 16 away from the pipe 10, and a service tap 20 is secured to the threaded portion 18.

The T-connector 14 is shown in greater detail in FIG. 2. The threaded portion 18 includes threads 22 in a cylindrical partially threaded opening 24 or bore. The internally partially threaded opening 24 extends from a top to a bottom of the housing to the pipe surface 12. The service tap 20 has an opening 26 or passageway which passes through the wall of the threaded portion 18. A cap 28 is provided to seal the service tap 20.

A test plug 30 preferably formed from aluminum, includes a threaded portion 32 which mates with the threaded portion 22 of the bore. A shank 34 is provided between a head 33 and one end of the threaded portion 32. As shown, the shank preferably includes the threaded portion 32. A base 36 is provided on the other end of the threaded portion 32. The base 36 includes a swivel mechanism 38 and a foot 40. The foot 40 includes a rubber bottom 42. The test plug 30 is axially movable within the partially threaded bore.

The swivel mechanism 38 may be any suitable bearing or other low friction interface. Preferably, the swivel mechanism 38 includes a ball and socket arrangement located in an axial center of the base 36 and foot 40. The base 36 defines a socket for receiving a ball 44. The foot 40 also includes a socket for receiving the ball 44. The bottom 42 may be rubber, neoprene or any other suitable material which may be pressed against the outer surface or wall 12 without damaging the pipe 10.

Figure 3:
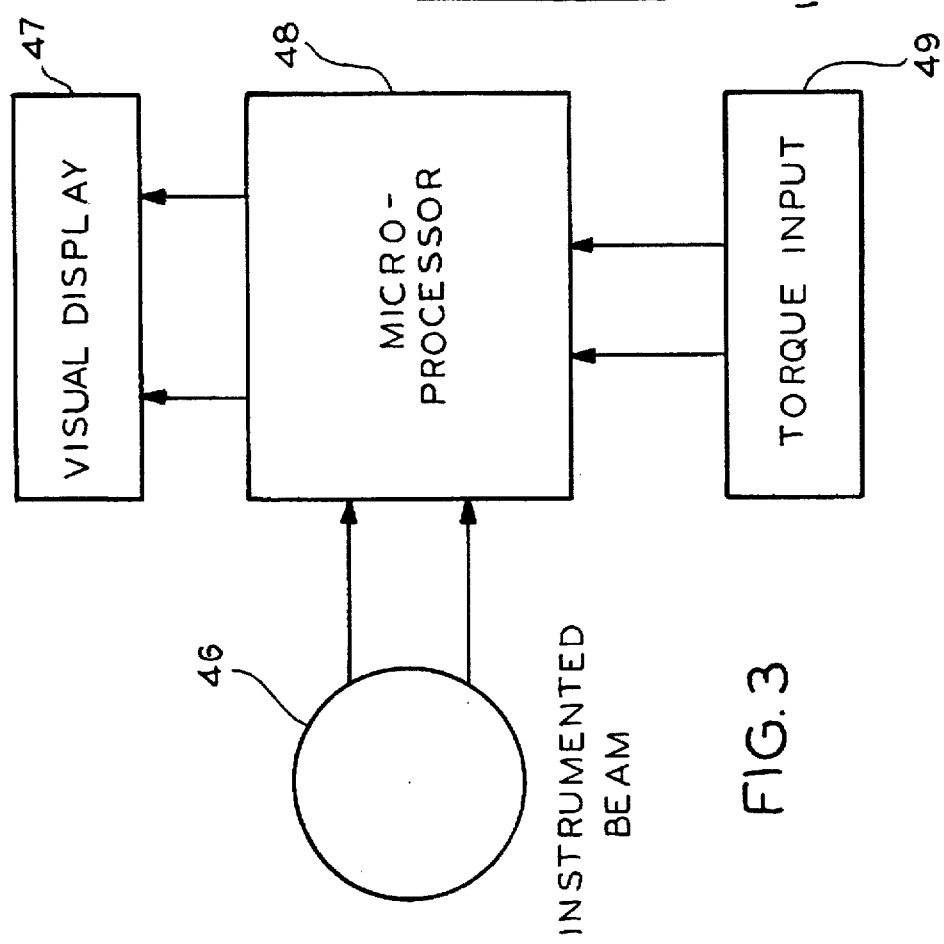
FIG. 3 is a block diagram illustrating functions of a suitable torque wrench, partially shown in FIG. 2, for carrying out the methods set forth herein.

The test plug 30 may be turned with a torque detection mechanism 45 such as a programmable electronic torque wrench or any other suitable device. As shown in FIG. 3, the torque detection mechanism 45 preferably includes an instrumented torque beam 46, a visual display 47 and/or an audible torque alarm, such as a beeper (not shown), a presettable torque limit and detection function via a suitably programmed microprocessor 48 and a torque input mechanism 49.

The instrumented torque beam 46 may be a rotary torque cell mechanism adapted with a handle and electronics to provide and detect 0–25 ft. lbs. of torque. Conventional torque wrenches typically have capabilities of applying and detecting 15–250 ft. lbs. with poor resolution given the large range of torque being detected and applied. In contrast, the instant torque application and detection mechanism can accurately detect smaller ranges of torque and provide visual and audible feedback for the operator. However, a Mountz Model M15250F torque wrench, manufactured by Mountz Inc., Pennsylvania can be used.

The rotary torque cell, such as a GSE 0328240-00500, sold by GSE, Inc., Michigan provides an electronic output on data lines to the microprocessor 48 or suitable microcomputer to indicate the amount of torque being applied. A preset torque limit is input to the microprocessor 48 through the torque input mechanism 49 such as a dial or keypad on the handle. The visual display 47 displays the set amount of torque and also displays the amount of torque being applied. The microprocessor 48 stores the preset torque limit and monitors the actual torque being applied through the data lines to the rotary torque cell. When the microprocessor 48 determines that the actual torque equals the preset limit, a visual indication is provided on the display device 47. In addition, an audible alarm is activated to notify the operator that the maximum torque limit has been reached. Hence the visual display 47 provides a torque readout to allow the operator to determine the amount of torque being applied and can provide an alarm message when a relatively small preset torque limit is being exceeded.

In use, the plug 30 is inserted into the threaded portion 18 and turned to axially move the test plug 30 until the bottom 40 presses against the pipe outer surface 12. The tight fit of the plug serves to seal the opening 24. The electronic torque wrench is then used to turn the plug 30 to a preset torque. Generally, a torque of about 15 ft. lbs is adequate to test the joint 16 without destroying it. The torque wrench serves as a torque detecting mechanism since it determines the amount of torque being applied. Once the predetermined amount of torque is applied, the joint is visually inspected to see whether cracks have formed. As such, the fusion joint is tested by axially moving the test plug to exert an upward force on the fusion joint and the torque detecting mechanism 45 determines the amount of force being applied. The operator inspects the joint or interface for a failure. Alternatively, a shear test may be used to test the strength of the joint.

The heat fusion joint 16 is made by heating the T-connector saddle to about 500 degrees Fahrenheit, as well known in the art. Standards, such as ASTM standard D2513, provide procedures for fusing the T-connector to the main pipe.

An alternate embodiment of the invention is shown in FIG. 4. FIG. 4 shows a test plug 50 having a threaded portion 52, a shank 54 on one end of the threaded portion 52, and a base section 56 at the other end of the threaded portion 52. The shank 54 includes a fluid channel 58. The fluid channel 58 is in fluid communication with an isolated volume A and facilitates the placing of a predetermined amount of fluid pressure on the fusion joint 17. In this manner, the fusion joint 17 can also be pneumatically tested to detect slight leaks in the joint. Although air pressure is preferred, other fluids such as light gases or liquids may also be used.

The fluid channel 58 extends axially down through the shank 54 and radially outward toward a periphery of the base 56 of the shank. A foot 60 is the same as foot 40 (FIG. 2). The fluid channel 58 couples with a valve arrangement 62 which preferably includes a ball 64 and spring 66 combination to regulate fluid flow through the channel 58. A head 68 of the shank 54 is suitably designed with a tube 69 to swage connect to an air pressure source. The valve is designed to bias the ball 64 against a shoulder to seal the channel unless enough pressure to overcome the spring bias is applied to the ball 64. The spring is affixed in the channel 58 by a plate that allows fluid to pass through. However, any suitable connector and valve arrangement can also be used such as a conventional Schroeder valve.

The fluid channel 58 preferably includes several radially extending passages 70a–d (70c–d not shown) which are displaced at 90° intervals in the same horizontal plane. These passages 70a–d exit the shank portion adjacent the base 56. The multiple passages 70a–d provide for a relatively fast and equal pressurization of the isolated area A about the periphery of the base of the plug to provide pneumatic pressure on the saddle fusion joint. It will be recognized that the channel 58 and its passages 70a–d can be any suitable number and in any suitable orientation.

Like the test plug 30, a swivel mechanism 72, such as a ball and socket arrangement is used to avoid unnecessary damage to the pipe. A rubber foot 74 serves the same purpose as the bottom 42 in FIG. 2.

In operation, the plug 50 is screwably tightened with a predetermined torque, such as 15 ft. lbs, in a similar way as was previously described with respect to the test plug 30 in FIG. 2. After the predetermined torque is applied, a predetermined amount of fluid pressure, such as 60 psi of air pressure, is also provided through the valve 62 through the fluid channel 58 and its passages 70a–d to pressurize the isolated area about the foot of the plug to pressurize the fusion interface. The pressure in combination with the mechanical loading allows fusion joints with the minor stress failures to be detected.

The failure of a joint can be detected through the use of a fluid pressure detection gauge (not shown), such as an air pressure gauge, which is coupled to the end 68. The pressure detection gage may be an analog or digital pressure detection gage which can detect changes in pressure. For example, if 60 lbs per square inch (psi) of pressure is applied through the plug, and the gage reads less than 60 psi, then a leak allowing air to pass through the joint is detected. The mechanical stress applied by the torque force provides a minimum loading requirement similar to the plug in FIG. 2.

The advantages of this invention are now apparent. For example, the heat fused joint may be suitably tested before the pipe is cut. The pipe is not damaged during the testing process due to the rubber foot. A mechanical load or combination of mechanical and fluid pressure load is applied through the test plug to detect even small leaks. An accurate torque detection mechanism allows small of torque to be detected and applied.

While the principles of the invention have been described above in connection with specific apparatus and applications, it is to be understood that this description is made only by way of example and not as a limitation on the scope of the invention. As one of ordinary skill in the art will appreciate, modification and variations may be made to the fusion interface test system without departing from the scope and spirit of the invention. By way of example only, the swivel mechanism may not include a double socket arrangement but instead may be a single socket with the foot being the socket rotatable about the shank. Also, the plugs may be made from material other than aluminum, such as plastic, steel or a combination of metal and plastic. The torque may also be applied with a drill and socket arrangement or any other suitable arrangement.

We claim:

1. A fusion joint test system for a saddle connector interface with a pipe, the saddle connector having a housing with an internally threaded cylindrical bore, a saddle portion extending from a bottom of the housing having a fusion joint with the pipe, at least one arm projecting from a side of the housing and having a hollow passageway extending into the cylindrical bore, said test system comprising:

a torque detecting mechanism; and a test plug axially movable within the bore, said plug having a head for cooperating with said torque detecting mechanism, a threaded shank with a first end connected to said head and cooperating with the threaded cylindrical bore, and a rotatable swivel base section operatively connected to a second end of said shank, said swivel base having a rubber foot, whereby the fusion joint is tested by axially moving the test plug to exert a force on the fusion joint and the torque detecting mechanism determines the amount of force being applied.

2. A fusion joint test system of claim 1 wherein said threaded shank defines a fluid channel to allow fluid pressure to be applied to the fusion joint.

3. A fusion joint test system of claim 2 wherein the fluid channel is coupled to a valve mechanism to regulate the flow of fluid through the fluid channel.

4. A fusion joint test system for a saddle connector interface with a pipe, the saddle connector having a housing with an internally threaded cylindrical bore, a saddle portion extending from a bottom of the housing having a fusion joint with the pipe, at least one arm projecting from a side of the housing and having a hollow passageway extending into the cylindrical bore, said test system comprising:

a test plug axially movable within the bore, said plug having a head, a threaded shank with a first end connected to said head and cooperating with the threaded cylindrical bore, and a rotatable swivel base section operatively connected to a second end of said shank, said swivel base having a rubber foot, whereby the rubber foot substantially conforms to the surface of the pipe and the swivel base section substantially prevents the rubber foot from slipping on the pipe when in contact with the pipe.

5. The fusion joint test system of claim 4 wherein said threaded shank defines an air channel to allow air pressure to be applied to the fusion joint.

6. The fusion joint test system of claim 5 wherein the air channel includes a valve mechanism to regulate the flow of air through the channel.

7. A method of testing a saddle fusion joint on a pipe, the saddle being connected to a housing with an internally threaded cylindrical bore, the saddle extending from a bottom of the housing and heat fused with the pipe, at least one arm projecting from a side of the housing, and the housing having a hollow passageway extending into the cylindrical bore, the method comprising:

screwing a swivel test plug into the internally threaded cylindrical bore of the housing until said plug makes contact with the pipe;

tightening said test plug with a predetermined torque to exert an upward force on the fusion interface;

applying a predetermined amount of fluid pressure through the swivel test plug to apply pressure to the saddle fusion joint; and inspecting the fusion interface for an interface failure.

* * * * *